United States Patent [19]

Kärnä et al.

[11] Patent Number: 4,662,991
[45] Date of Patent: May 5, 1987

[54] METHOD FOR DETERMINING THE PROPERTIES OF FIBER PULP

[75] Inventors: Anssi Kärnä; Heikki Liimatainen, both of Inkeroinen, Finland

[73] Assignee: Oy Tampella Ab, Tampere, Finland

[21] Appl. No.: 576,322

[22] Filed: Feb. 2, 1984

[30] Foreign Application Priority Data

Feb. 17, 1983 [FI] Finland .................................. 830534

[51] Int. Cl.[4] .......................... D21C 1/08; G01N 7/10
[52] U.S. Cl. .................................... 162/49; 73/61 R; 73/61.4; 162/198; 162/263
[58] Field of Search .................... 73/61 R, 63, 61.4; 162/198, 49, 258, 263, DIG. 10

[56] References Cited

U.S. PATENT DOCUMENTS 3,688,563 9/1972 Enarsson et al. .................... 73/63
3,838,594 10/1974 Kesler .................................. 162/263

FOREIGN PATENT DOCUMENTS 1000505 3/1983 U.S.S.R. .............................. 162/198

OTHER PUBLICATIONS

McGill, "Measurement and Control in Papermaking", Adam Holger Ltd., Bristol; 1980, pp. 285–286.

Primary Examiner—Steve Alvo
Attorney, Agent, or Firm—Roylance, Abrams, Berdo & Goodman

[57] ABSTRACT

A method of determining the properties of fiber pulp by separating a batch of a predetermined volume, by measuring its temperature, and by filtering water from it by means of a pressure difference. In accordance with the present invention, substantially all the water is filtered off from the pulp mixture, an air flow is produced through the filtered pulp cake by means of a pressure difference, the resisting effect of the pulp cake on the flow of air is measured, and the pulp cake is weighed, whereafter the properties of the pulp are calculated on the basis of the measurements, from mathematical models developed for this purpose.

The apparatus developed for carrying out the method according to the invention has a vessel equipped with a stirrer for the specimen, a device for measuring the temperature of the specimen, means for directing the specimen onto the wire and for removing the water through the wire by means of a pressure difference, a device for measuring the pressure difference or through-flow produced across the wire and the pulp layer on the wire, and devices for registering the obtained measurements and for the output of the properties of the pulp. For directing a batch of a predetermined volume from the vessel into the measuring vessel placed against the wire, this determination apparatus has a specific portioning device, and the device has been fitted not to register the pressure difference or through-flow produced across the wire and the pulp layer on the wire, until substantially all the water has been removed from the pulp layer filtered onto the wire. In addition, this apparatus has means for removing the pulp layer from the wire and a device for weighing the pulp layer.

9 Claims, 2 Drawing Figures

METHOD FOR DETERMINING THE PROPERTIES OF FIBER PULP

BACKGROUND OF THE INVENTION

The present invention relates to a method and apparatus for determining the properties of fiber pulp by taking a fiber pulp batch of a predetermined volume, by measuring its temperature and by filtering water from it by means of a pressure difference.

From publications Svensk Papperstidning, 9 (1977) 265-284 and Pulp & Paper 55 (1981) 72-75 there are known various methods and devices for determining the properties of fiber pulp. In these methods the consistency of the fiber suspension is first measured and, when necessary, the fiber suspension is diluted to a consistency suitable for the measuring. In the first-mentioned publication it is noted that the suitable consistency is approximately 1 g/liter for unrefined fibers and approximately 0.25 g/liter for refined fibers and groundwood pulp. In the second publication the fiber suspension must be diluted to a consistency of approximately 0.5%. The method according to the first-mentioned publication is based on measuring the pressure difference produced across the fiber layer filtered onto the wire while the flow of liquid through the wire is constant, and the method according to the second-mentioned publication is based on measuring the flow velocity of liquid through the fiber bed while it is subjected to constant pressure. In addition, in both methods the temperature of the fiber suspension is measured, and other properties of the fiber pulp can be calculated on the basis of the measurements obtained.

By the above-mentioned methods it is not possible to determine the consistency of the fiber suspension, and this has to be analyzed separately before the beginning of the determination. In addition, these prior known determination methods can be applied only to very dilute fiber suspensions, and thus they seldom can be applied directly to specimens taken from the process flow, but the specimen must first be diluted to the suitable consistency. Also, these prior known measuring methods do not provide reliable results when the properties of pulps having a high shive content, for example pulps from under the pulpstone of a pulp grinder, are being determined. Furthermore, these methods of determination are relatively sensitive to air present in the fiber suspension; in general, the air must first be removed from the fiber suspension before the determination is started.

The object of the present invention is to provide a method and device for determining the properties of fiber pulp, a method by which the properties of a fiber pulp, including its consistency, can be determined, for example, directly from the process flow, without prior dilution, by which it is also possible to determine the properties of pulps having a high shive content, such as pulps from under the pulpstone in a pulp grinder, and in which air possibly present in the fiber suspension does not in any way hamper the measuring.

SUMMARY OF THE INVENTION

According to the present invention and in a manner deviating from the above-mentioned prior known methods, water is allowed substantially to filter out of the fiber suspension in order to form a pulp cake on the wire and only thereafter is the pressure difference across the filtered pulp cake or the amount of air flowing through it, or both, measured. In accordance with the present invention the resisting effect on the flow of air, of the pulp cake filtered onto the wire is thus measured, which is done advantageously either by measuring the amount of air flow while the pressure difference across the pulp cake is constant or by measuring the produced pressure difference across the pulp cake while the air flow is constant. A state of equilibrium suitable for the measuring is created rather soon after substantially all the water has been removed from the pulp, i.e. in practice after, for example, 15-150 seconds from the beginning of the filtering.

By the method according to the present invention it is also possible to determine the consistency of fiber suspension by measuring the temperature of a fiber suspension batch of a predetermined volume and the effect of the fiber suspension batch on air flow, as well as by weighing the pulp cake filtered onto the wire. It has been surprisingly observed that by using the method and apparatus according to the invention it is thus possible to determine both the consistency and the quality of the pulp with relative reliability within a wide temperature, consistency and grinding-degree range both in a laboratory and also directly from the process flow, and by means of the method and apparatus according to the invention it is also possible to determine several paper technical properties of pulps having a high shive content, such as pulps from under the pulpstone of pulp grinders. The method of determination according to the invention is very rapid and precise, since it takes simultaneously into account the temperature of a pulp suspension batch of a predetermined volume, the weight of the suction-filtered pulp cake, and the effects on the final result of the pressure difference produced across the suction-filtered pulp cake, and on the basis of these measurements it is then possible to calculate mathematically the above-mentioned properties of the pulp. By measuring the three above-mentioned factors, namely the temperature, the weight of the pulp cake and the effect of the pulp cake on the flow of air through it, from a pulp specimen of a constant volume, it is, according to the studies carried out, possible to determine with surprising precision the following properties, among others: consistency, degree of grinding, wet strength, tensile index, burst index, bonding power, scattering of light, and fine-material content. The method according to the present invention is not dependent on the consistency of the pulp suspension, and the consistency of the pulp may vary within quite wide ranges, for example from 0.1% to 3%. By the method according to the invention it is thus possible to measure and calculate the properties of fiber pulp directly from, for example, the pulps from under the pulpstone of a grinder, the consistency of these pulps being typically within the range 1-2%.

Since the pressure difference or through-flow produced across the pulp cake is not measured until substantially all the water has been removed through the wire, the air possibly present in the pulp suspension cannot in any way affect the measurement. The detemination method according to the present invention is thus very precise.

In accordance with the present invention, advantageously either the amount of air flowing through the filtered pulp cake while the pressure difference between the two sides of the pulp cake is constant, or the pressure difference produced across the filtered pulp cake while the flow of air through the pulp cake is constant, is measured. It is, of course, possible to measure both the pressure difference and the amount of air flow, but by maintaining one of them constant both the measuring and the further procedures are simplified. The above-mentioned pressure difference is advantageously produced by creating a vacuum on that side of the wire which is opposite the pulp cake.

DESCRIPTION OF THE PREFERRED EMBODIMENTS

Figure 1:
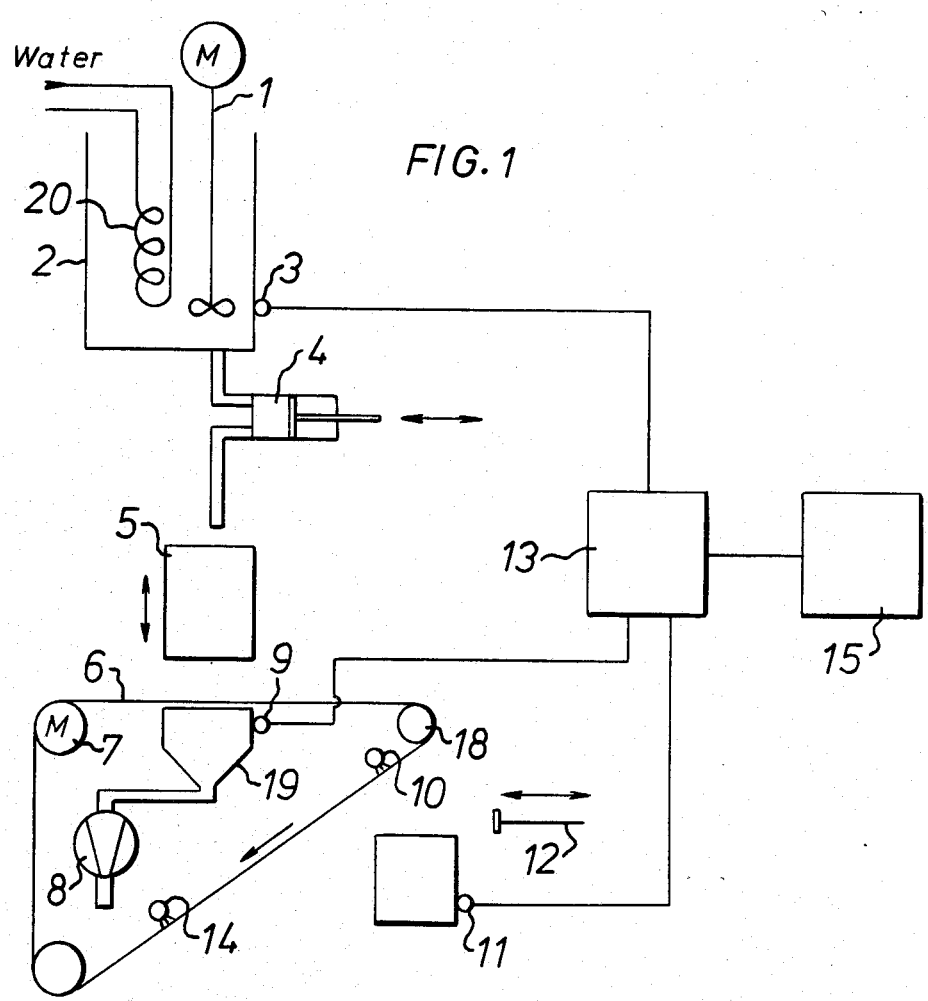
FIG. 1 is a schematic vertical representation of a preferred embodiment of the invention.

According to FIG. 1, the specimen to be studied is first introduced into a specimen vessel 2 provided with a stirrer 1, and having a thermometer 3 and a heat exchanger 20, by means of which the specimen can, when necessary, be heated or cooled. By means of a piston-operated portioning device 4 a batch of fiber suspension of a precisely controlled volume is transferred from the vessel 2 into a measuring vessel 5, which is a cylinder open both upwards and downwards. Before the specimen batch of a controlled volume is lowered into the measuring vessel 5, the vessel is lowered in such a way that its lower edge comes tightly against the surface of the endless wire 6. On the opposite side of the wire 6 in relation to the measuring vessel 5, i.e. on its lower side, there is a suction chamber 19 connected to a vacuum pump 8, a pressure meter 9 being connected to the suction chamber 19 in order to measure the vacuum prevailing in it. By means of the vacuum pump 8 the water is sucked out of the specimen batch in the measuring vessel 5 through the wire 6 into the suction chamber 19 below, and after substantially all the water has been sucked out of the pulp cake filtered onto the wire 6, the vacuum prevailing in the suction chamber 19 is measured by means of the meter 9.

After the measuring of the vacuum the measuring vessel 5 is raised so as to separate from the wire 6 in such a way that the wire length on which the pulp cake is can be moved forward around the turning roll 18 by means of the motor 7 moving the endless wire 6, in order to drop the pulp cake on the wire 6 onto the weighing device 11 below the turning roller 18. The detaching of the pulp cake from the wire 6 can be ensured by means of an air nozzle 10 inside the wire loop, fitted at a point subsequent to the turning roller 18 and aimed towards the wire, and the after-cleaning of the wire is implemented by means of a water nozzle 14 also fitted inside the wire loop, at a point subsequent to the air nozzle 10 and aimed towards the wire 6. After the weighing the pulp cake is removed from the weighing device 11 by means of a scraper 12.

The measurements given by the thermometer 3, the vacuum meter 9 and the weighing device 11 are transferred to the registering device 13 and from there further to the control and output unit 15, by means of which, applying separately determined models, the original consistency of the pulp, its degree of fineness, its paper technical properties and possible other characteristic figures describing the quality of the pulp are calculated from the registered measurement data. The operations of the portioning device 4, the measuring vessel 5, the motor 7 and the scraper 12 are also controlled by means of the control and output unit 15.

Figure 2:
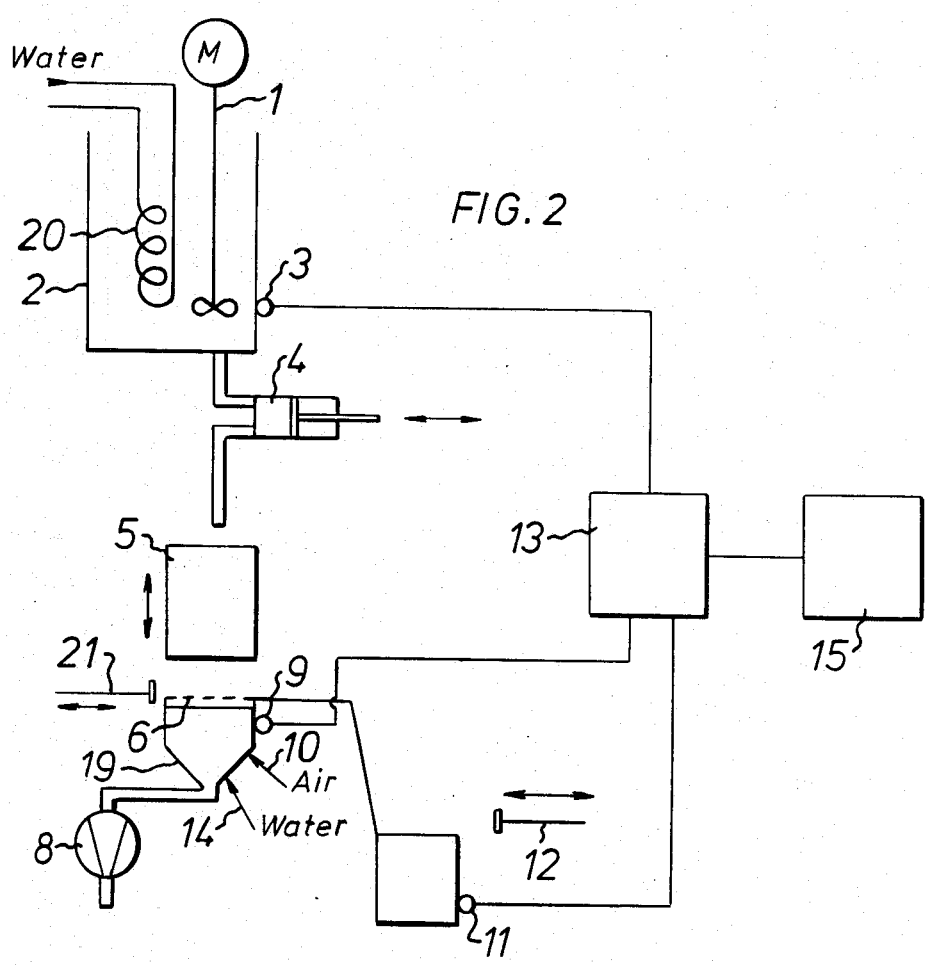
FIG. 2 is a similar representation of an alternative embodiment.

The embodiment depicted in FIG. 2 deviates from the embodiment shown in FIG. 1 in that, instead of an endless wire, a fixed, plane wire 6 is used, through which the specimen batch is filtered. From this fixed wire 6 the filtered pulp cake is removed by means of a scraper 21 moving reciprocatingly along the upper surface of the wire; by means of the scraper the pulp cake is detached from the wire 6 and transferred onto the weighing device 11 below.

A conduit 10 is connected to the suction chamber 19 below the wire 6 in order to feed compressed air into the suction chamber 19; this compressed air fed below the wire 6 detaches the pulp cake filtered onto the wire 6, before the pulp cake is removed from the wire 6 by means of the scraper 21. To the suction chamber 19 there is additionally connected a water feed pipe 14, by means of which water can be fed under pressure into the suction chamber 19 or sprayed towards the wire 6 in order to remove any fibers possibly adhering to the wire 6, before the next specimen batch is filtered through the wire 6. de The invention is described below in greater detail by way of an example.

EXAMPLE

The consistencies of 21 coarse screened pulps from under the pulpstone were determined by a standard method. The results are shown for each specimen in Table 1 below.

TABLE 1

| Pulp | Laboratory-determined consistency % | Weight g | Vacuum mmHg | Temperature °C. |
|---|---|---|---|---|
| 1 | 1.14 | 22.90 | 139.0 | 48.0 |
| 2 | 1.35 | 31.25 | 141.0 | 22.5 |
| 3 | 0.64 | 12.95 | 149.5 | 22.0 |
| 4 | 1.72 | 37.70 | 138.5 | 39.0 |
| 5 | 1.14 | 23.75 | 142.5 | 46.0 |
| 6 | 0.90 | 17.80 | 131.5 | 46.8 |
| 7 | 0.91 | 18.90 | 165.5 | 33.0 |
| 8 | 1.60 | 35.50 | 144.5 | 50.0 |
| 9 | 0.83 | 16.90 | 152.0 | 22.0 |
| 10 | 1.12 | 23.95 | 131.0 | 37.5 |
| 11 | 0.64 | 12.05 | 149.5 | 38.0 |
| 12 | 1.44 | 33.20 | 117.5 | 50.5 |
| 13 | 0.75 | 15.05 | 167.5 | 24.8 |
| 14 | 1.09 | 24.40 | 152.0 | 26.0 |
| 15 | 1.35 | 28.00 | 148.5 | 35.5 |
| 16 | 1.03 | 19.95 | 193.0 | 41.8 |
| 17 | 0.68 | 11.60 | 225.0 | 46.5 |
| 18 | 1.48 | 31.80 | 148.0 | 27.0 |
| 19 | 0.47 | 8.05 | 238.5 | 34.0 |
| 20 | 0.71 | 12.15 | 264.5 | 41.5 |
| 21 | 1.19 | 28.50 | 130.0 | 20.0 |
| min | 0.47 | 8.05 | 117.5 | 20.0 |
| $\bar{X}$ | 1.056 | 22.207 | 160.429 | 35.82 |
| max | 1.72 | 37.07 | 264.5 | 50.5 |
| variation coefficient$^x$, % | 32.91 | 39.17 | 23.85 | 28.64 |

The same specimens were subjected to the determination method according to the present invention, and the temperature of the sample, the weight of the filtered pulp cake and the vacuum created under the filtered pulp cake were registered and entered into the above Table 1. On the basis of these measurements, a regression model was sought for the consistency, the dependent variable being the consistency and the independent variables being the three above-mentioned measurements, namely weight, vacuum and temperature. By means of regression analysis, the following model was obtained for the consistency:

$$\text{Consistency} = -0.140 + 245 \times 10^{-4} \text{ weight} - 254 \times 70^{-7} \times \text{vacuum} \times \text{temperature} + 115 \times 10^{-6} \times \text{weight} \times \text{vacuum} + 173 \times 10^{-4} \times \text{temperature} - 151 \times 10^{-6} \times \text{temperature}^2$$

$$^x\text{Variation coefficient} = \frac{s}{\bar{x}} \cdot 100, \, s = \text{standard deviation}, \, \bar{x} = \text{mean}$$

The degree of explanation obtained for the model of consistency was in this case 99.4%, which $= 100 \times R^2$, where R is the joint correlation coefficient of the model. In this case the joint correlation coefficient obtained for the consistency is 99.7%.

By means of this model it is thus possible to calculate the consistency of an unknown specimen by measuring its temperature, the weight of the filter cake obtained from it by filtration, and the vacuum produced under the filtered pulp cake.

Thus, if 28° C. is obtained as the temperature of the unknown specimen and 35 g as the weight of the pulp cake, and the measured vacuum is 150 mmHg, the consistency of this unknown pulp specimen can be calculated by substituting these values in the above formula, in which case the final result obtained is a consistency of 1.58%.

The same way as for consistency, other properties of the pulp can also be calculated on the basis of the obtained measurements by creating a regression model on the basis of results obtained by standard methods, and the desired property can then be calculated from the model on the basis of the measurements obtained from the unknown specimen.

In the examples above, the filtering and measuring steps take place in immediate succession in the devices depicted in FIGS. 1 and 2 with the aid of the same pressuredifference producing apparatus.

The filtering and measuring steps can also take place completely separately from each other and in separate units. In such a case there may be for the filtration of the water a separate device which creates a vacuum or a pressure difference, the water-removing capacity of the device being regulatable in the desired manner independently of later steps. In this manner the water can be removed from the pulp cake in a manner most advantageous for the measuring. Respectively, at the air-flow measuring device the control of the air flow, or respectively the pressure difference or vacuum, can be achieved in the manner most advantageous for the measuring, regardless of how the removal of the water is controlled. In this case water is first filtered from the fiber suspension in a filtering device, in which a pulp cake is formed from the fibers. The pulp cake is thereafter transferred into a measuring device, where the resisting effect of the pulp cake on the through-flow of air is measured. Thereafter the pulp cake is weighed and the properties of the fiber pulp are calculated. An apparatus made up of separate measuring units can also be implemented so as to automatic, if so desired.

What is claimed is:

1. A method of determining a property of a fibrous pulp suspension selected from the group consisting of consistency, degree of grinding, wet strength, tensile strength, burst index, bonding power, scattering of light, and fine material content, which method comprises taking a sample of a predetermined volume of said fibrous pulp suspension, then filtering the sample to remove water from said sample by means of a pressure difference, and producing a pulp cake, passing a flow of air through the filtered pulp cake by means of a pressure difference and measuring the resisting effect of the pulp cake on the flow of air, then measuring the weight of the pulp cake, measuring the temperature of said fibrous pulp suspension or said sample to determine the temperature of said sample of predetermined volume, and determining at least one of said properties using the measured temperature, resisting effect and weight of the pulp.

2. A method according to claim 1, in which the resisting effect of the pulp cake on the flow of air is measured as a pressure difference while the flow of air across the pulp cake is kept constant.

3. A method according to claim 1, in which the resisting effect of the pulp cake on the flow of air is measured as the amount of the air flow while the pressure difference across the pulp cake is kept constant.

4. A method according to claim 1, in which the pressure difference for producing the air flow is obtained by sucking air from one side of the pulp cake while normal atmospheric pressure prevails on the other side of the pulp cake, and that the resisting effect of the pulp cake on the flow of air is measured as the vacuum produced.

5. A method according to claim 1, in which the filtering of the water from the pulp mixture and the measuring of the resisting effect of the filtered pulp cake on the flow of air take place in immediate succession, in which case the flow of air through the pulp cake is started when water has been sufficiently filtered from it, and that the resisting effect of the pulp cake on the flow of air is measured after a certain time has elapsed from the starting of the filtering.

6. A method according to claim 1, in which the measuring is carried out at a stage at which a sufficient equilibrium for the measuring has been created.

7. A method according to claim 6, in which the measuring is carried out when water has been filtered from the fiber pulp for about 30 seconds.

8. The method of claim 1 wherein the property determined is that of consistency.

9. The method of claim 8 wherein the temperature of the fibrous pulp suspension is measured.

* * * * *